(12) United States Patent
Yamashita et al.

(10) Patent No.: US 7,056,961 B2
(45) Date of Patent: Jun. 6, 2006

(54) ADHESIVE COMPOSITION FOR DENTURE BASE RELINING MATERIAL AND DENTAL CURABLE COMPOSITION

(75) Inventors: Mitsuhiro Yamashita, Tokuyama (JP); Toshio Kawaguchi, Tokuyama (JP); Masanao Hashiguchi, Okuyama (JP)

(73) Assignees: Tokuyama Corporation, Yamaguchi-Ken (JP); Tokuyama Dental Corporation, Tokyo (JP)

( * ) Notice: Subject to any disclaimer, the term of this patent is extended or adjusted under 35 U.S.C. 154(b) by 371 days.

(21) Appl. No.: 10/433,420

(22) PCT Filed: Dec. 3, 2001

(86) PCT No.: PCT/JP01/10551

§ 371 (c)(1),
(2), (4) Date: Jun. 4, 2003

(87) PCT Pub. No.: WO02/45660

PCT Pub. Date: Jun. 13, 2002

(65) Prior Publication Data

US 2004/0048948 A1 Mar. 11, 2004

(30) Foreign Application Priority Data

Dec. 4, 2000 (JP) .............................. 2000-368200
Dec. 13, 2000 (JP) .............................. 2000-379367

(51) Int. Cl.
*A61K 6/083* (2006.01)
*A61C 5/00* (2006.01)

(52) U.S. Cl. ...................................... 523/116; 523/120

(58) Field of Classification Search ............... 523/116, 523/120; 433/217.1, 228.1
See application file for complete search history.

(56) References Cited

U.S. PATENT DOCUMENTS

| | | | |
|---|---|---|---|
| 5,290,172 A | | 3/1994 | Sakuma et al. |
| 5,407,973 A | | 4/1995 | Hasegawa et al. |
| 5,962,550 A | * | 10/1999 | Akahane et al. ............. 523/116 |
| 6,472,454 B1 | * | 10/2002 | Qian ........................... 523/116 |

FOREIGN PATENT DOCUMENTS

| | | |
|---|---|---|
| JP | 58-72509 A | 4/1983 |
| JP | 58-201628 A | 11/1983 |
| JP | 59-36604 A | 2/1984 |
| JP | 59-134705 A | 8/1984 |
| JP | 61-50906 A | 3/1986 |
| JP | 61-126007 A | 6/1986 |
| JP | 61-134306 A | 6/1986 |
| JP | 61-136562 A | 6/1986 |
| JP | 62-22804 A | 1/1987 |
| JP | 62-149609 A | 7/1987 |
| JP | 63-17815 A | 1/1988 |
| JP | 3-76702 A | 4/1991 |
| JP | 3-206012 A | 9/1991 |
| JP | 9-241304 A | 9/1997 |
| JP | 10-231228 A | 9/1998 |
| JP | 11-335222 A | 12/1999 |

OTHER PUBLICATIONS

Robert J. Clemens, Chemical Reviews, vol. 86, No. 2, Apr. 1986, pp. 241-318.

* cited by examiner

*Primary Examiner*—Tae H. Yoon
(74) *Attorney, Agent, or Firm*—Birch Stewart Kolasch & Birch LLP

(57) ABSTRACT

An adhesive composition for a denture base relining material which comprises an organic solvent containing no halogen atoms such as ethyl acetate, ethyl formate or acetone, a polymer such as a copolymer of methyl methacrylate and ethyl methacrylate, and a radical polymerizable monomer such as tetramethylolmethane tetramethacrylate; and a curable composition which comprises a radical polymerizable monomer, an organic peroxide such as benzoyl peroxide, a tertiary amine compound such as diethyl-p-toluidine or dipropyl-p-toluidine, and a hydroxycarboxylic acid such as malic acid or citric acid.

The adhesive composition for a denture base relining material does not contain a halogen-atom-containing organic solvent whose harmful effect has been pointed out. Further, the composition has satisfactory adhesive properties and good operability and causes no degradation in the appearance of a denture base even if it sticks to an area on the surface of the denture base other than a contact area. The dental curable composition is widely used as dental materials having little surface unpolymerized layer and good curability, e.g., dental cement, a composite resin, a resin for crown and a denture base relining material.

8 Claims, No Drawings

ADHESIVE COMPOSITION FOR DENTURE BASE RELINING MATERIAL AND DENTAL CURABLE COMPOSITION

This application is the national phase under 35 U.S.C. § 371 of PCT International Application No. PCT/JP01/10551 which has an International filing date of Dec. 3, 2001, which designated the United States of America.

TECHNICAL FIELD

This invention relates to an adhesive for a denture base relining material which is used to bond a denture base and a denture base relining material together; and a dental curable composition which can be suitably used as a dental material such as a denture base relining material.

BACKGROUND ART

When one wears a denture for a long time, the denture becomes unfitted to an oral membrane due to bone resorption and/or deformation of the surface of the membrane. For this reason, means for restoring an optimum fit of the denture by relining the surface of the unfitted denture base with a denture base relining material is clinically employed.

Illustrative examples of a material used in the denture base include an acrylic resin, a polycarbonate resin, and a polysulfone resin. Of these, the acrylic resin is the most commonly used. Meanwhile, as a material used as the relining material, a mixture of monomers and polymers of (meth)acrylic resins is predominantly used. To bond the relining material to the denture base effectively, a method of applying an organic solvent such as methylene chloride which contains halogen atoms to the surface of the denture base is generally employed.

However, when the denture base and the relining material are made of different materials, sufficient bonding strength may not be obtained through the application of the organic solvent containing halogen atoms alone. For this reason, as adhesives for general purpose applications, adhesives comprising organic solvents containing halogen atoms and a variety of polymers have been developed.

As such adhesives, an adhesive using a chlorine-based organic solvent and a polycarbonate resin (refer to JP-A 61-50906 and JP-A 61-134306), an adhesive using a combination of a chlorine-based organic solvent and an aromatic polyester polymer or a polyester carbonate (refer to JP-A-61-136562), an adhesive using a combination of methylene chloride, a polystyrene resin and a polymethyl methacrylate (refer to JP-A 58-72509), and an adhesion assistant using a combination of methylene chloride, a polycarbonate resin, a polymethyl methacrylate and a multifunctional methacrylate (refer to JP-A 10-231228) and other adhesives are known. In these adhesives, methylene chloride is the most widely used as the organic solvent containing halogen atoms since it has a low boiling point, evaporates fast and easy to handle.

However, in recent years, more stringent control of the organic solvent containing halogen atoms has been increasingly demanded in view of environmental loads and harmful effects. For example, the Ministry of Health and Welfare has provided "Guideline for Residual Solvents in Drugs" to all prefectural and city governments in 1998. In the guideline, residual solvents in drugs are classified into classes 1 to 3 based on their toxicity. According to the classification, methylene chloride used in the above adhesives is classified into the class 2 since it is a solvent which does not causes an unacceptable level of toxicity but shows a certain level of toxicity, and it is defined as a solvent whose residual level in drugs should be regulated so as to protect patients from possible harmful effects. Further, other chlorine-based organic solvents usable as adhesives for denture base relining materials are also classified into the class 1 or 2. Hence, an adhesive for a denture base relining material which uses no chlorine-based organic solvent is desired.

Further, as an adhesive using no chlorine-based organic solvent, an adhesive comprising an organic solvent having a boiling point of 30 to 250° C. and a thermoplastic polyhydroxy ether is disclosed as an adhesive for a polysulfone-based resin and a dental acrylic resin in JP-A 62-149609. The adhesive takes long time to dry after application and has lower bonding strength than an adhesive using a chlorine-based organic solvent.

Further, the following can be said of all polymer-containing adhesives. That is, bonding durability when such adhesives are used is not necessarily satisfactory. Further, there arises a problem that when the surface of a denture base coated with the treating agent is partially left uncovered with a relining material and the uncovered portion is exposed after completion of bonding operation, the uncovered portion (hereinafter referred to as "surface coated with an excess of treating material or adhesive") may be whitened, thereby degrading esthetics of the denture base.

Meanwhile, as dental materials such as a denture base relining material, dental cement, a composite resin and a resin for crown, compositions comprising a radical polymerizable monomer which can be polymerized in the presence of a radical, e.g., (meth)acrylate, an organic peroxide and a tertiary amine compound are widely used due to their characteristic that they are polymerized quickly at temperatures ranging from room temperature to a temperature in an oral cavity so as to form cured products.

For example, a direct method denture base relining material is a material for repairing a base of a denture which becomes unfitted to the palate of a patient as a result of long-term use so as to restore the denture to a reusable condition. To use the material, a paste which is polymerized and cured at temperatures ranging from room temperature to a temperature in an oral cavity is applied on a denture base, the denture is directly inserted into the oral cavity of a patient and fitted to the surface of an oral membrane, and the paste is polymerized and cured while kept in the oral cavity so as to restore the denture base. As the relining material, the above compositions which are cured around room temperature are widely used. Heretofore, as such a relining material, a powder-liquid two-component material comprising a powder component which is a mixture of a powdery synthetic resin such as a polymethyl methacrylate (hereinafter abbreviated as "PMMA"), a polyethyl methacrylate (hereinafter abbreviated as "PEMA") and a copolymer of methyl methacrylate and ethyl methacrylate (hereinafter abbreviated as "PMMA-PEMA") and an organic peroxide and a liquid component which is a mixture of a radical polymerizable monomer such as methyl methacrylate and a tertiary amine compound has been used.

In the case of such a two-component material, when the two components were mixed together, radicals are produced easily at temperatures ranging from room temperature to a temperature in an oral cavity, and polymerization and curing start after a lapse of given time from the mixing. Further, upon contact with the powder component, the above liquid component not only dissolves a portion of the powder component in a short time but also permeates the synthetic resin powder so as to swell it. Thus, the viscosity of the mixture can be adjusted properly, and a clinical operation can be facilitated advantageously.

However, the above direct method denture base relining material has a problem that the material undergoes inhibition of surfacial curing caused by oxygen in the air and/or foreign matter in an oral cavity at the time of curing, whereby an insufficiently cured portion is liable to be formed. If such an insufficiently cured portion (hereinafter referred to as "surface unpolymerized layer") exists, it causes such problems that a relined denture is liable to discolor and that foreign matter in an oral cavity is liable to stick to the denture and renders it unsanitary.

Such a problem of formation of the surface unpolymerized layer is a problem common to dental curing compositions containing radical polymerizable monomers, organic peroxides and tertiary amine compounds and has been desired to be improved.

As a method for preventing formation of the surface unpolymerized layer of the curable composition and reducing a surface unpolymerized amount (amount of unpolymerized monomer present on the surface), a method of applying an air barrier agent and a method of using an accelerator are known. The method of applying an air barrier agent is a method of covering the surface of a radical polymerizable monomer with an oxygen-shielding film formed by application of the air barrier agent during curing of the radical polymerizable monomer so as to prevent inhibition of polymerization caused by oxygen in the air. As the air barrier agent, an aqueous solution of a polyvinyl alcohol (refer to JP-A 58-201628), a composition prepared by adding an organic peroxide to a polyvinyl alcohol aqueous solution (refer to JP-A 59-36604), a composition comprising a low-molecular-weight polyethylene glycol and a high-molecular-weight polyethylene glycol (refer to JP-A 59-134705), and a composition comprising an aqueous solution of a water-soluble oxygen-shielding polymer, a water-soluble reducing agent and a surfactant (refer to JP-A 9-241304) are known. Meanwhile, the method of using an accelerator is a method in which a curable composition such as a denture base relining material is cured in an oral cavity and then a denture is immersed in a hot aqueous solution having an accelerator dissolved therein so as to cause the curable composition to undergo secondary curing. As commercial accelerators, a product which generates carbon dioxide upon dissolution in water and removes oxygen dissolved in the water and a product characterized in that a water-soluble polymerization initiator is dissolved in hot water have been actually used.

DISCLOSURE OF THE INVENTION

An object of the present invention is to provide an adhesive composition for a denture base relining material using an organic solvent containing no halogen atoms which is safer than a chlorine-based organic solvent.

Another object of the present invention is to provide an adhesive composition for a denture base relining material which is excellent in operability at the time of use, initial bonding strength, bonding durability and esthetics of a surface coated with an excess of adhesive, in other words, causes no deterioration in the appearance of a denture base even if sticking to the surface of the denture base other than a bonding surface.

Still another object of the present invention is to provide a dental curable composition which inherently has a small surface unpolymerized amount by itself without using an air barrier agent or an accelerator to reduce the surface unpolymerized amount to an acceptable level and also has good curability.

Still another object of the present invention is to provide a method of relining a denture base by use of the above adhesive composition for a denture base relining material of the present invention and dental curable composition of the present invention.

Other objects and advantages of the present invention will become apparent from the following description.

According to the present invention, firstly, the above objects and advantages of the present invention are achieved by an adhesive composition for a denture base relining material which composition comprises 100 parts by weight of organic solvent containing no halogen atoms, 0.1 to 35 parts by weight of polymer and 0.1 to 100 parts by weight of radical polymerizable monomer.

According to the present invention, secondly, the above objects and advantages of the present invention are achieved by an adhesive composition which is an adhesive for a denture base relining material and which comprises 100 parts by weight of organic solvent containing no halogen atoms, 0.1 to 35 parts by weight of polymer and 0.1 to 100 parts by weight of radical polymerizable monomer.

According to the present invention, thirdly, the above objects and advantages of the present invention are achieved by a dental curable composition which comprises a radical polymerizable monomer, an organic peroxide, a tertiary amine and a hydroxycarboxylic acid.

Further, according to the present invention, fourthly, the above objects and advantages of the present invention are achieved by a method of relining a denture base which comprises the steps of applying the adhesive composition of the present invention on a surface of a denture where the denture makes contact with an oral membrane so as to form a coating film comprising a polymer and a radical polymerizable monomer on the surface, and then applying and curing the dental curable composition of the present invention on the coating film so as to form a prosthetic portion on the denture base.

PREFERRED EMBODIMENTS OF THE INVENTION

Firstly, an adhesive composition for a denture base relining material of the present invention will be described hereinafter.

Although the present invention is not bound to theory, it is assumed that in the adhesive composition of the present invention, a logical fitting force is imparted to between a denture base and a relining material by addition of a polymer and bonding strength and bonding durability are improved by addition. of a polymerizable monomer since the polymerizable monomer not only permeates the denture base but also mixes with the pre-curing relining material so as to be polymerized and cured at the time of curing of the relining material, while operability and esthetics of a surface coated with an excess of the adhesive composition are rendered good by controlling the amounts of these components.

The adhesive composition for a denture base relining material of the present invention is prepared by adding specific amounts of polymer and radical polymerizable monomer to an organic solvent containing no halogen atoms. When only a polymer is added to the organic solvent containing no halogen atoms, the following problem occurs. That is, when the adhesive composition is applied to the surface of a denture base where the denture base makes contact with an oral membrane, the polymer is deposited after evaporation of the organic solvent, and the deposited polymer whitens the surface of the denture base and causes pits and projections on the surface, thereby degrading the esthetics of the surface coated with an excess of the adhesive composition. Meanwhile, when only a radical polymerizable monomer is added to the organic solvent containing no halogen atoms, bonding durability by thermal shock is liable to deteriorate although an improvement in adhesive strength is seen.

The organic solvent containing no halogen atoms which is used in the present invention is not particularly limited and may be any organic solvent which has no halogen substituents in a molecular skeleton, dissolves a radical polymerizable monomer component and dissolves or swells a polymer component. It is preferred to use organic solvents which do not belong to the classes 1 and 2 described in the foregoing "Guideline for Residual Solvents in Drugs" from the viewpoint of safety. Further, it is preferred to use an organic solvent which has high solubility of a polymer since the adhesive composition itself becomes in solution form and good coatability (operability) can be obtained. Illustrative examples of organic solvents containing no halogen atoms which are suitably used in the present invention include hydrocarbons, alcohols, ethers, ketones and carboxylates. Preferably, hydrocarbons having 5 to 8 carbon atoms, alcohols having 1 to 5 carbon atoms, ethers having 4 to 8 carbon atoms, ketones having 3 to 6 carbon atoms and carboxylates having 2 to 6 carbon atoms are used.

Specific examples thereof include hydrocarbons such as heptane and pentane; alcohol compounds such as ethanol, 1-propanol, 2-propanol, 1-butanol and 2-butanol; ethers such as diethyl ether, tetrahydrofuran and t-butyl methyl ether; ketones such as acetone, methyl ethyl ketone, and methyl isobutyl ketone; and carboxylates such as ethyl formate, methyl acetate, ethyl acetate, propyl acetate and isopropyl acetate. These organic solvents containing no halogen atoms can be used alone or in admixture of two or more. Of these organic solvents containing no halogen atoms, those having a boiling point of 20 to 150° C., particularly 30 to 100° C. are particularly suitable because low-boiling-point organic solvents having volatility are dried quickly and easy to handle. Further, mixed solvents of ketones and carboxylates are preferred since durability after bonding is excellent. Having these characteristics, a combination of acetone and ethyl formate or a combination of acetone and ethyl acetate can be the most suitably used.

As the polymer used in the present invention, a commonly available polymer such as a poly(meth)acrylate, a polycarbonate and a polyester are used without any restrictions. A homopolymer or copolymer of a (meth)acrylic acid alkyl ester compound is suitably used since it dissolves into a mixture of the organic solvent containing no halogen atoms and the radical polymerizable monomer so as to form a uniform solution having good operability such as coatability and shows high bonding strength to a poly(meth)acrylate which is generally used as a denture base. Specific examples of polymers which can be suitably used in the present invention include homopolymers or copolymers of acrylates such as methyl acrylate, methyl methacrylate (hereinafter abbreviated as "MMA"), ethyl acrylate, ethyl methacrylate (hereinafter abbreviated as "EMA"), propyl acrylate, propyl methacrylate, butyl acrylate and butyl methacrylate. An adhesive composition using a homopolymer or copolymer of an ester of (meth)acrylic acid and an alkyl alcohol having 1 to 4 carbon atoms out of the above polymers has a characteristic that bonding strength and bonding durability are high. Of these, a copolymer of methyl acrylate and ethyl acrylate or a copolymer of methyl methacrylate and ethyl methacrylate is preferred, and the copolymer of methyl methacrylate and ethyl methacrylate is most preferably used since bonding strength and bonding durability are particularly high.

The weight average molecular weights of these polymers are not particularly limited. However, the weight average molecular weights are suitably 10,000 to 2,000,000, particularly suitably 100,000 to 1,000,000 since when the polymers have such weight average molecular weights, they dissolve into a mixture of the organic solvent containing no halogen atoms and the radical polymerizable monomer easily, and a surface coated with an excess of the adhesive has a uniform thickness and good esthetics.

The amount of the polymer contained in the adhesive composition of the present invention must be 0.1 to 35 parts by weight, preferably 0.5 to 10 parts by weight, based on 100 parts by weight of the organic solvent containing no halogen atoms. When the amount is smaller than 0.1 parts by weight, sufficient bonding strength cannot be attained supposedly because a physical fitting force imparted by addition of the polymer is insufficient, while when the amount is larger than 35 parts by weight, the viscosity of the adhesive becomes high, whereby its operability is lowered.

The radical polymerizable monomer used in the adhesive composition of the present invention is not particularly limited as long as it is a monomer having a polymerizable unsaturated bond such as a vinyl group. For example, compounds such as divinylbenzene, alkyl vinyl ethers and (meth)acrylates can be used. (Meth)acrylate-based radical polymerizable monomers are suitably used because they are highly soluble in the polymer components, have high affinity for a denture and a relining material, some of them can be expected to be copolymerized with these constituent materials, and high bonding strength can also be obtained.

As the (meth)acrylic radical polymerizable monomers, known (meth)acrylic radical polymerizable monomers which can be used in dental restorative materials can be generally used without any restrictions. Specific examples of such radical polymerizable monomers include monofunctional and multifunctional radical polymerizable monomers enumerated in the following (1) to (4). In the following compound designations, "(meth)acrylate" represents "methacrylate" or "acrylate".

(1) Monofunctional (Meth)acrylic Radical Polymerizable Monomers

Methacrylates such as methyl methacrylate, ethyl methacrylate, isopropyl methacrylate, hydroxyethyl methacrylate, 2-hydroxproply methacrylate, 3-chloro-2-hydroxypropyl methacrylate, tetrahydrofurfuryl methacrylate and glycidyl methacrylate, and acrylates corresponding to these methacrylates; or acrylic acid, methacrylic acid, p-methacryloyloxybenzoic acid, N-2-hydroxy-3-methacryloyloxypropyl-N-phenylglycine, 4-methacryloyloxyethyltrimellitic acid and an anhydride thereof, 6-methacryloyloxyhexamethylenemalonic acid, 10-methacryloyloxydecamethylenemalonic acid, 2-methacryloyloxyethyldihydrogenphosphate, 10-methacryloyloxydecamethylenedihydrogenphosphate and the like, and compounds represented by formulae (1) to (7) and exemplified as monofunctional (meth)acrylic radical polymerizable monomers in the following section of a dental curable composition.

(2) Bifunctional (Meth)acrylic Radical Polymerizable Monomers (2-1) Aromatic-Compound-Based Monomers 2,2-bis(methacryloyloxyphenyl)propane, 2,2-bis[4-(3-methacryloyloxy)-2-hydroxypropoxyphenyl] propane (hereinafter abbreviated as "bis-GMA"), 2,2-bis(4-methacryloyloxyphenyl)propane, 2,2-bis(4-methacryloyloxypolyethoxyphenyl)propane (hereinafter abbreviated as "D-26E"), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxydiethoxyphenyl)-2-(4-methacryloyloxy triethoxyphenyl)propane, 2-(4-methacryloyloxydipropoxyphenyl)-2-(4-methacryloyloxy triethoxyphenyl)propane, 2,2-bis(4-methacryloyloxypropoxyphenyl)propane, 2,2-bis(4-methacryloyloxyisopropoxyphenyl)propane, and acrylates corresponding to these methacrylates.

(2-2) Aliphatic-Compound-Based Monomers

Ethylene glycol dimethacrylate, diethylene glycol dimethacrylate, triethylene glycol dimethacrylate (hereinafter abbreviated as "3G"), butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these methacrylates; acrylic anhydride, methacrylic anhydride, 1, 2-bis(3-methacryloyloxy-2-hydroxypropoxy)ethyl, di(2-methacryloyloxypropyl) phosphate, and the like.

(3) Trifunctional (Meth)acrylic Radical Polymerizable Monomers

Methacrylates such as trimethylolpropane trimethacrylate, trimethylolethane trimethacrylate, pentaerythritol trimethacrylate, trimethylolmethane trimethacrylate and the like, acrylates corresponding to these methacrylates, and the like.

(4) Tetrafunctional (Meth)acrylic Radical Polymerizable Monomers

Tetramethylolmethane tetramethacrylate, pentaerythritol tetramethacrylate, acrylates corresponding to these methacrylates, and the like.

These radical polymerizable monomers can be used alone or in combination of two or more. Of the above radical polymerizable monomers, the multifunctional (meth)acrylic radical polymerizable monomers are preferably used, and multifunctional (meth)acrylic radical polymerizable monomers having at least three functional groups are particularly preferably used since initial bonding strength is further enhanced.

The amount of the radical polymerizable monomer must be 0.1 to 100 parts by weight based on 100 parts by weight of the organic solvent containing no halogen atoms. When the amount is smaller than 0.1 parts by weight, bonding strength does not improve, while when it is larger than 100 parts by weight, a surface coated with an excess of the adhesive composition becomes sticky, and its esthetics are lowered. Further, the radical polymerizable monomer is preferably added in an amount of at least ½ of the weight of the polymer so as to dissolve the polymer efficiently and to improve the esthetics of the surface coated with an excess of the adhesive.

The adhesive composition of the present invention may contain additives such as a colorant and a perfume in such amounts that do not impair the effect of the present invention.

A method for preparing the adhesive composition of the present invention is not particularly limited, and it can be prepared by weighing predetermined amounts of the components and mixing them together. Further, a method of using the adhesive composition is not particularly limited, either. For example, the adhesive composition is used in a method for forming an adhesive coating film on a given surface of a denture which comprises applying the adhesive composition of the present invention on the surface of the denture where the denture makes contact with an oral membrane so as to form the coating film comprising a polymer and a radical polymerizable monomer on the surface. For example, more specifically, the adhesive composition of the present invention is applied thinly by a brush or the like on the surface of a denture figured by a stamp bar or the like where the denture makes contact with an oral membrane and then dried, and a denture base relining material is then placed thereon and cured. The adhesive composition of the present invention exhibits a particularly high effect when used for bonding a relining material to a denture base composed essentially of a (meth)acrylic resin.

Next, a dental curable composition of the present invention will be described.

The dental curable composition of the present invention has characteristics that a surface unpolymerized amount at the time of curing is small without using an air barrier agent or an accelerator and that a cured product has high durability. Of the above dental curable compositions of the present invention, a dental curable composition containing a polymer has characteristics that the viscosity of the composition can be adjusted freely and that the composition exhibits high strength when cured.

A radical polymerizable monomer used in the dental curable composition of the present invention is not particularly limited as long as it is radical-polymerizable. For example, a radical polymerizable monomer having an acryloyloxy group and/or a methacryloyloxy group which is generally used in a dental material can be used without restrictions. Specific examples of such a radical polymerizable monomer include those shown in the following (I) to (IV).

(I) Monofunctional (Meth)acrylic Radical Polymerizable Monomers

Methyl (meth)acrylate, ethyl (meth)acrylate, isopropyl (meth)acrylate, hydroxyethyl (meth)acrylate, tetrahydrofurfuryl (meth)acrylate, glycidyl (meth)acrylate, and a (meth) acrylate compound represented by any of the following formulae (1) to (7).

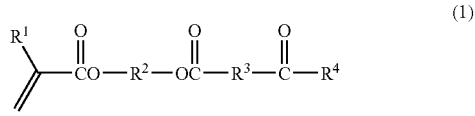

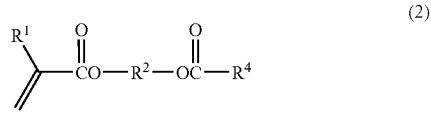

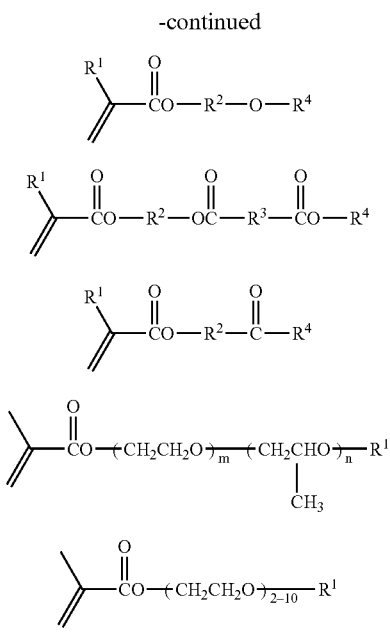

wherein R¹ represents a hydrogen atom or a methyl group, R² and R³ each independently represent an alkylene group, R⁴ represents an alkyl group, m represents 0 or 1, and n represents an integer of 1 to 10 (m+n is an integer of 2 to 10). The above alkylene group as R² or R³ is not particularly limited but is preferably an alkylene group having 2 to 6, carbon atoms.

As the monofunctional (meth)acrylic radical polymerizable monomer, a compound represented by the above formula (1) is preferred.

In consideration of solubility or a swelling property when used in combination with a polymer, R² and R³ in the above formula (1) each independently are preferably an alkylene group having 1 to 6 carbon atoms such as a methylene group, an ethylene group, an ethylidene group, a trimethylene group, a propylene group, a tetramethylene group, a 1-methyltrimethylene group, a 1,2-dimethylethylene group and a hexamethylene group, more preferably an alkylene group having 2 to 6 carbon atoms, particularly preferably an alkylene group having 2 to 4 carbon atoms. Further, due to the same reason, the alkyl group as R⁴ in the above formula (1) is an alkyl group having 1 to 4 carbon atoms such as a methyl group, an ethyl group, a propyl group or a butyl group and is suitably the methyl group or the ethyl group.

(II) Difunctional (Meth)acrylic Radical Polymerizable Monomers (i) Aliphatic Compounds Ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, 1,9-nonamethylene glycol di(meth)acrylate, 1,10-decanediol di(meth)acrylate, (meth)acrylic anhydride; and 1,2-bis(3-methacryloxy-2-hydroxypropoxy)ethyl, di(2-methacryloxyethyl)phosphate, di(3-methacryloxypropyl)phosphate, and acrylates thereof.

(ii) Aromatic Compounds 2,2-bis(methacryloxyphenyl)propane, 2,2-bis[4-(3-methacryloxy)-2-hydroxypropoxyphenyl] propane, 2,2-bis(4-methacryloxyethoxyphenyl)propane, 2,2-bis(4-methacryloxydiethoxyphenyl)propane, 2,2-bis(4-methacryloxytetraethoxyphenyl)propane, 2,2-bis(4-methacryloxypentaethoxyphenyl)propane, 2,2-bis(4-methacryloxydipropoxyphenyl)propane, 2-(4-methacryloxyethoxyphenyl)-2-(4-methacryloxydiethoxy phenyl)propane, 2-(4-methacryloxydiethoxyphenyl)-2-(4-methacryloxytriethoxy phenyl)propane, 2-(4-methacryloxydipropoxyphenyl)-2-(4-methacryloxy triethoxyphenyl)propane, 2,2-bis(4-methacryloxypropoxyphenyl)propane, 2,2-bis(4-methacryloxyisopropoxyphenyl)propane, and acrylates thereof.

(III) Trifunctional (Meth)acrylic Radical Polymerizable Monomers

Trimethylolpropane tri(meth)acrylate, trimethylolethane tri(meth)acrylate, pentaerythritol tri(meth)acrylate, and trimethylolmethane tri(meth)acrylate.

(4) Tetrafunctional (Meth)acrylic Radical Polymerizable Monomers

Pentaerythritol tetramethacrylate, and pentaerythritol tetraacrylate.

The above radical polymerizable monomers can be used alone or in combination of two or more. Further, any combinations of radical polymerizable monomers having different numbers of functional groups can be selected freely.

Of the above radical polymerizable monomers, a mixture of a monofunctional (meth)acrylic radical polymerizable monomer and a multifunctional (meth)acrylic radical polymerizable monomer is suitably used in consideration of a balance between the brittleness and mechanical properties such as flexural strength and flexural modulus of a cured product resulting from curing of the dental curable composition of the present invention. Further, a mixture of a monofunctional (meth)acrylic radical polymerizable monomer and a difunctional (meth)acrylic radical polymerizable monomer is suitably used because a balance among physical properties can be achieved easily. In this case, as the ratio of the monofunctional (meth)acrylic radical polymerizable monomer to the difunctional (meth)acrylic radical polymerizable monomer, a weight ratio of 5:95 to 95:5, particularly 20:80 to 80:20 is suitably used.

Further, when the dental curable composition of the present invention is used in such an application as a direct method denture base relining material which is used in an oral cavity, a (meth)acrylate compound represented by the above formula (1) is particularly suitably used as the monofunctional (meth)acrylic radical polymerizable monomer because it causes a weak irritating odor, gives low stimuli to an oral membrane and a skin and reduces heat generation at the time of polymerization. Further, as the difunctional (meth) acrylic polymerizable monomer used in combination with the compound, 1,6-hexamethylenediol dimethacrylate, 1,9-nonamethylenediol dimethacrylate, 1,10-decanediol dimethacrylate or the like can be suitably used in consideration of an odor, stimuli to a skin and a membrane and the like. Further, when the dental curable composition is used in such an application, the compound represented by the above formula (1) preferably constitutes 5 to 95 wt % of all radical polymerizable monomers. Specific examples of the compound represented by the above formula (1) which is suitably used for such a purpose include the following compounds M-AE-1 to M-AE-8.

M-AE-1;
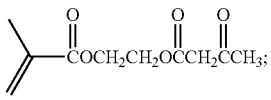

M-AE-2;
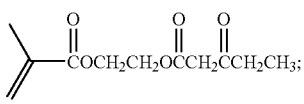

M-AE-2;
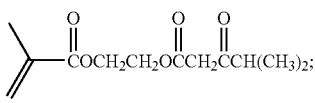

M-AE-4;
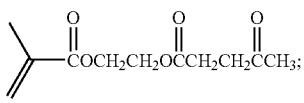

M-AE-5;
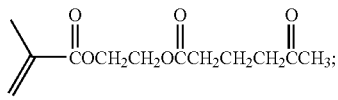

M-AE-6;
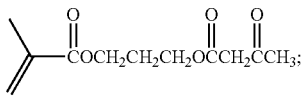

M-AE-7;
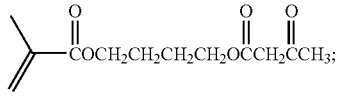

M-AE-8;
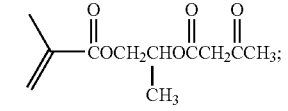

A number of compounds represented by the above formula (1) are commercially available, and the compounds can be produced easily by the following first and second methods.

As the first method, the compound can be produced easily by reacting a corresponding (meth)acrylic acid hydroxyalkyl ester with a corresponding carboxylic acid so as to cause dehydration condensation. According to the first method, for example, 1 mole of (meth)acrylic acid hydroxyalkyl ester and 1 mole of carboxylic acid are reacted with each other in toluene in the presence of an acid catalyst and a polymerization inhibitor under heating for 2 hours while produced water is distilled out. Then, the obtained reaction product is washed with a sodium carbonate aqueous solution and then dried over sodium sulfate, and the solvent is then distilled out under a reduced pressure, whereby the target compound can be obtained. Further, as the second method, a method comprising reacting a corresponding (meth)acrylic acid hydroxyalkyl ester with diketene {R. J. Clemens, Chemical Review, 86, 241 (1986)} is mentioned. According to the method, for example, 1 mole of hydroxyalkyl(meth)acrylate, 1 g of triethylamine and 1 g of butylhydroxytoluene are dissolved in 500 ml of anhydrous ethyl acetate. To this solution, 88 g (1.05 moles) of diketene is added dropwise under agitation in one hour so as to cause a reaction. Then, the reaction mixture is heated under reflux for 2 hours, cooled, washed with diluted hydrochloric acid and then with water and dried over sodium sulfate, and then the solvent is distilled out under a reduced pressure, whereby the target compound can be obtained.

As an organic peroxide used in the dental curable composition of the present invention, any organic peroxide capable of generating radicals upon contact with a tertiary amine can be used without any restrictions. Specific examples of organic peroxides which are suitably used include benzoyl peroxide, 2,4-dichlorobenzoyl peroxide, and dilauroyl peroxide. Although a suitable amount of the organic peroxide varies according to the type of the organic peroxide and therefore cannot be limited to a particular amount, it is preferably 0.05 to 5 parts by weight, more preferably 0.1 to 2 parts by weight, based on 100 parts by weight of all radical polymerizable monomers.

As a tertiary amine compound used in the dental curable composition of the present invention, a known compound can be used without particular limitations. Specific examples of tertiary amine compounds which are suitably used include anilines such as N,N-dimethylaniline, N,N-diethylaniline, N,N-dipropylaniline, N,N-dibutylaniline and N-methyl,N-β-hydroxyethylaniline, toluidines such as N,N-dimethyl-p-toluidine, N,N-diethyl-p-toluidine, N,N-dipropyl-p-toluidine, N,N-dibutyl-p-toluidine, p-tolyldiethanolamine and p-tolyldipropanolamine, anisidines such as N,N-dimethylanisidine, N,N-diethyl-p-anisidine, N,N-dipropyl-p-anisidine and N,N-dibutyl-p-anisidine, morpholines such as N-phenylmorpholine and N-tolylmorpholine, bis(N,N-dimethylaminophenyl)methane, bis(N,N-dimethylaminophenyl)ether, and the like. These amine compounds may be used as salts with hydrochloric acid, phosphoric acid, and organic acids such as acetic acid and propionic acid.

Of the above tertiary amine compounds, N,N-diethyl-p-toluidine, N,N-dipropyl-p-toluidine, p-tolyldiethanolamine and p-tolyldipropanolamine are suitably used because they have high polymerization activity, cause a low stimulus and do not have a strong odor. Further, when it is necessary to store a tertiary amine compound for a long time in the form of a mixture with a radical polymerizable monomer, it is preferable from the viewpoint of storage stability to use N,N-diethyl-p-toluidine or N,N-dipropyl-p-toluidine.

The tertiary amine compound is used in an amount of preferably 0.05 to 5 parts by weight, more preferably 0.1 to 2 parts by weight, based on 100 parts by weight of all radical polymerizable monomers.

Specific examples of suitable combinations of the organic peroxides and the tertiary amine compounds include a combination of benzoyl peroxide and N,N-diethyl-p-toluidine, a combination of benzoyl peroxide and N,N-dipropyl-p-toluidine, a combination of benzoyl peroxide and p-tolyldiethanolamine, and a combination of benzoyl peroxide and p-tolyldipropanolamine. Of these, when it is necessary to store a tertiary amine compound for a long time in the form of a mixture with a radical polymerizable monomer, a combination of benzoyl peroxide and N,N-diethyl-p-toluidine and a combination of benzoyl peroxide and N,N-dipropyl-p-toluidine are the most preferable from the viewpoint of storage stability.

The most significant feature of the dental curable composition of the present invention is that it contains a hydroxycarboxylic acid compound. By containing the hydroxycarboxylic acid compound, the dental curable composition becomes less liable to undergo formation of a surface unpolymerized layer when polymerized and cured, and a surface unpolymerized amount can be reduced. The hydroxycarboxylic acid compound used in the dental curable composition of the present invention is not particularly limited as long as it is a compound having a carboxyl group and a hydroxyl group. A compound having a hydroxyl group at an α position in a carboxyl group is preferably used because its effect of reducing a surface unpolymerized amount is high. Illustrative examples of hydroxycarboxylic acid compounds which are suitably used include citric acid, malic acid, tartaricacid, glycolic acid, gluconic acid, α-oxyisobutyric acid, 2-hydroxypropionic acid, 3-hydroxybutanoic acid, 4-hydroxybutanoicacidanddimethylolpropionicacid. These hydroxycarboxylic acid compounds may be used alone or in combination of two or more.

The amount of the hydroxycarboxylic acid compound is not particularly limited. However, in view of the effect, it is preferably 0.005 to 2 parts by weight, particularly preferably 0.1 to 1 part by weight, based on 100 parts by weight of all radical polymerizable monomers.

The dental curable composition of the present invention can be used for applications such as repairing of defective or lost tooth, splinting of a mobile tooth, rearrangement, and relining of a denture base. More specifically, the dental curable composition of the present invention can be suitably used as a material for crown such as a selfcuring resin for repairing a denture, a selfcuring resin for crown, a quick-curing selfcuring resin, a hard resin for crown or a dental resin for correction or as a material for a denture base such as a selfcuring resin for relining a denture base or a selfcuring resin for an individual tray.

In addition to the above essential components, the dental curable composition of the present invention may also contain a synthetic resin powder; an inorganic filler; an alcohol or plasticizer such as ethanol, dibutyl phthalate or dioctyl phthalate; a polymerization inhibitor such as butylhydroxytoluene or methoxyhydroquinone; a dye, a pigment, a perfume, and the like according to the above applications so as to improve flowability and to control various physical properties of a cured product and curability to be obtained.

It is preferable that the dental curable composition of the present invention be used in combination with the adhesive composition of the present invention. More specifically, a denture base can be relined by applying the adhesive composition of the present invention on a surface of a denture where the denture makes contact with an oral membrane so as to form a coating film comprising a polymer and a radical polymerizable monomer on the surface, and applying and curing the dental curable composition of the present invention on the coating film so as to form a prosthetic portion on the denture base.

Particularly, when the dental curable composition of the present invention is used as a direct method denture base relining material such as a selfcuring resin for relining a denture base, it is suitable to add a polymer powder to the composition because the material is required to have moderate viscosity. The polymer powder used in this case is not particularly limited as long as it is a polymer which can be dissolved in a radical polymerizable monomer wholly or partially or swollen by a radical polymerizable monomer. In general, in view of chemical stability and transparency, a powder of a polymethyl methacrylate, polyethyl methacrylate, polybutyl methacrylate, polystyrene or copolymer thereof is suitably used. Of these, the polyethyl methacrylate or copolymer thereof is particularly preferably used since the polyethyl methacrylate is swollen by the compound represented by the above formula (1) particularly easily.

The molecular weight and particle diameter of the polymer constituting the polymer powder are not particularly limited. However, in consideration of the mechanical strength of a cured product to be obtained and solubility in and swellability with a radical polymerizable monomer, its molecular weight is preferably 50,000 to 1,000,000, and its average particle diameter is preferably 1 to 100 μm. Further, the polymer powder is used in an amount of preferably 50 to 500 parts by weight, particularly preferably 100 to 200 parts by weight, based on 100 parts by weight of all radical polymerizable monomers.

Since the dental curable composition of the present invention contains a chemical polymerization catalyst, polymerization starts when all components are mixed together. Therefore, it is commonly practiced that the components are stored separately before use of the dental curable composition so as to prevent the polymerization from starting and they are mixed together upon use of the composition. The way they are stored separately is not particularly limited as long as the polymerization does not start. For example, when the dental curable composition is used as a denture base relining material containing a polymer powder, it is suitable from the viewpoint of ease of weighing and handling each component that a powder component comprising the polymer powder and an organic peroxide in a predetermined ratio and a liquid component comprising a radical polymerizable monomer, a tertiary amine compound and a hydroxycarboxylic acid compound in a predetermined ratio are charged into two separate containers and stored and these two containers are used as kits. When such kits are used, predetermined amounts of powder and liquid are taken out of the corresponding containers at the time of use, mixed together, poured into a given form or put into shape, and then cured at room temperature or in an oral cavity.

Further, to this kit, a third container which contains an adhesive composition of the present invention may be combined.

EXAMPLES

Hereinafter, the adhesive compositions of the present invention will be described more specifically with reference to Examples 1 to 14. However, the present invention shall not be limited to these Examples.

Further, organic solvents containing no halogen atoms, polymers and radical polymerizable monomers used in Examples 1 to 14 and Comparative Examples 1 to 4 are as follows.
(a) Organic Solvents Containing No Halogen Atoms
  ethyl acetate, acetone, diethyl ketone, heptane
(b) Polymers
  polymethyl methacrylate (Mw=500,000, abbreviated as "PMMA")
  polyethyl methacrylate (Mw=500,000; abbreviated as "PEMA")
  methyl methacrylate/ethyl methacrylate copolymer {Mw=500,000, MMA/EMA molar ratio=30/70, abbreviated as "P(MMA-EMA)"}
(c) Radical Polymerizable Monomers
  methyl methacrylate (abbreviated as "MMA") triethylene glycol dimethacrylate (abbreviated as "3G")
  trimethylolpropane trimethacrylate (abbreviated as "TMPT")
  tetramethylolmethane tetramethacrylate (abbreviated as "TMMT")

Further, the operations, procedures for measurement and evaluation criteria of the surface properties, initial bonding strength and bonding durability of the adhesive composition after its application are as shown in the following (1) to (3).

(1) Surface Properties of Applied Adhesive Composition

An adhesive composition for a denture relining material of each of Examples and Comparative Examples was applied by a brush on a resin plate (20 mm×20 mm×2 mm) prepared from a material for a denture base (product of GC Co., Ltd., ACRON) made of a polymethyl methacrylate resin and having a surface polished with waterproof abrasive paper #320, and the surface properties of the resin plate were observed after the applied composition was dried. It can be said that the esthetics of the surface coated with an excess of the adhesive composition are good when the surface properties are uniform.

(2) Measurement of Bonding Strength

Resin plates (10 mm×10 mm×2 mm) were prepared by use of a resin for a denture base (product of GC Co., Ltd., trade name: ACRON) made of a polymethacrylate resin, polished with waterproof abrasive paper #320, and then immersed in water for 24 hours so as to form objects to be coated. After the surfaces of the objects were wiped and dried with KIMWIPE (product of CRESIA Corporation), the adhesive composition for a denture base relining material was applied by use of a brush. After the applied adhesive composition was left to stand until a solvent component in the adhesive composition evaporated and dried, a two-sided tape with a hole having a diameter of 3 mm was stuck on the dried composition so as to define a bonding area. Thereafter, a paste obtained by kneading a relining material made of an acrylic resin (product of TOKUYAMA Corp., TOKUSO REBASE FIRST TYPE) in a powder/liquid ratio described in an instruction manual was placed on the two-sided tape in an amount just enough to fill the hole and then crimped quickly with an acrylic attachment and cured at 37° C. in a wetting atmosphere, and the resulting objects were immersed in water at 37° C. for 24 hours so as to obtain samples for measurement. A measurement was made by use of a tensile testing machine (product of Shimadzu Corporation, AUTOGRAPH) at a crosshead speed of 1 mm/1 min. Bonding Strength was determined from an average of measurements made on 10 of the above samples.

(3) Evaluation of Bonding Durability

Thermal shock was repeatedly applied to samples for measurement of bonding strength which were prepared in the same manner as described above so as to evaluate bonding durability. The test was conducted by use of a thermal shock testing machine (product of THOMAS KAGAKU CO., LTD.) by repeating a cycle in which the sample was kept in water at 4° C. for 1 minute and then kept in hot water at 60° C. for 1 minute for 10,000 times. Ten of the samples after the thermal shock test were measured for tensile bonding strength, and an average of the measurements was taken as bonding strength after the durability test. Based on the tensile bonding strength of a sample which was not subjected to the heat cycle test, one showing a reduction in strength of not higher than 20% was rated as "◯", one showing a reduction in strength of higher than 20% but not higher than 40% was rated as "Δ", and one showing a reduction in strength of higher than 40% was rated as "X"

Example 1

5 parts by weight of P(MMA-EMA) as a polymer and 5 parts by weight of TMMT as a radical polymerizable monomer were added to and mixed with 100 parts by weight of ethyl acetate as an organic solvent containing no halogen atoms so as to prepare an adhesive composition for a denture base relining material of the present invention in the form of a solution.

When the surface properties after application of the adhesive composition for a denture base relining material were evaluated, they were good. Further, as a result of testing bonding of the composition to a relining material made of an acrylic resin (product of TOKUYAMA Corp., TOKUSO REBASE FIRST TYPE), bonding strength was 12.0 MPa, and bonding durability was ◯.

Examples 2 to 14

Adhesive compositions for denture base relining materials were prepared in the same manner as in Example 1 except that compositions shown in Table 1 were employed, and the properties of the adhesive compositions were evaluated. The results are shown in Table 1. Use of any of the adhesive compositions for denture base relining materials resulted in uniform surface properties, and all adhesive compositions showed high bonding strength and had bonding durability rated as ◯.

Comparative Example 1

A sample was prepared in accordance with the testing method (2) except that no adhesive composition for a denture base relining material was used, and bonding strength and bonding durability were evaluated. As a result, the bonding strength was as low as 6.9 MPa, and the bonding durability was X.

Comparative Examples 2 and 3

As examples containing neither polymers nor radical polymerizable monomers, adhesive compositions for denture base relining materials with compositions shown in Table 1 were prepared, and the properties of the adhesive compositions were evaluated in the same manner as in Example 1. As a result, both of the adhesive compositions gave uniform surface properties but had lower bonding strengths than Examples 1 to 14 and also had bonding durability rated as X.

Comparative Example 4

As an example containing no radical polymerizable monomer, an adhesive composition for a denture base relining material with composition shown in Table 1 was prepared, and the properties of the adhesive composition were evaluated in the same manner as in Example 1. In this case, a surface coated with the adhesive composition was whitened. Further, its bonding strength was as low as 7.9 MPa, and its bonding durability was rated as Δ.

Comparative Example 5

As an example containing no polymer, an adhesive composition for a denture base relining material with composition shown in Table 1 was prepared, and the properties of the adhesive composition were evaluated in the same manner as in Example 1. The adhesive composition showed high bonding strength of 10.5 MPa. However, after the thermal shock test, its strength was reduced to 5.2 MPa, and its bonding durability became X.

Comparative Example 6

The properties of an adhesive composition for a denture base relining material were evaluated in the same manner as in Example 1 except that a polymer was added in an amount of 0.01 parts by weight which was lower than the range of the present invention. With the amount, no effect caused by addition of the polymer was observed.

Comparative Example 7

The properties of an adhesive composition for a denture base relining material were evaluated in the same manner as in Example 1 except that a radical polymerizable monomer was added in an amount of 0.01 parts by weight which was lower than the range of the present invention. With the amount, no effect caused by addition of the radical polymerizable monomer was observed.

M-AE-2;

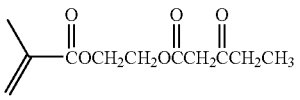

M-AE-3;

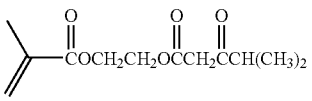

M-AE-4;

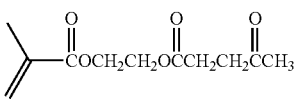

TABLE 1

| Ex. No. | Composition (parts by weight) | | | Surface Properties after Application | Adhesive Property (MPa) | | Evaluation of Durability |
|---|---|---|---|---|---|---|---|
| | Solvent | Polymer | Polymerizable Monomer | | Initial | After Thermal Shock Test | |
| Ex. 1 | Ethyl Acetate (100) | P (MMA-EMA) (5) | TMMT (5) | Uniform | 12.0 | 10.7 | ○ |
| Ex. 2 | Acetone (100) | P (MMA-EMA) (5) | TMMT (5) | Uniform | 13.0 | 10.9 | ○ |
| Ex. 3 | Ethyl Acetate (50)/Acetone (50) | P (MMA-EMA) (5) | TMMT (5) | Uniform | 14.0 | 11.2 | ○ |
| Ex. 4 | Ethyl Acetate (30)/Diethyl Ether (30) | P (MMA-EMA) (5) | TMMT (5) | Uniform | 12.1 | 10.4 | ○ |
| Ex. 5 | Ethyl Acetate (90)/Heptane (10) | P (MMA-EMA) (5) | TMMT (5) | Uniform | 11.5 | 10.1 | ○ |
| Ex. 6 | Ethyl Acetate (50)/Acetone (50) | PMMA (5) | TMMT (5) | Uniform | 11.9 | 10.6 | ○ |
| Ex. 7 | Ethyl Acetate (50)/Acetone (50) | PEMA (5) | TMMT (5) | Uniform | 12.5 | 10.6 | ○ |
| Ex. 8 | Ethyl Acetate (50)/Acetone (50) | PMMA (2.5)/PEMA (2.5) | TMMT (5) | Uniform | 12.0 | 10.5 | ○ |
| Ex. 9 | Ethyl Acetate (50)/Acetone (50) | P (MMA-EMA) (0.1) | TMMT (5) | Uniform | 12.5 | 10.3 | ○ |
| Ex. 10 | Ethyl Acetate (50)/Acetone (50) | P (MMA-EMA) (5) | MMA (5) | Uniform | 11.6 | 10.1 | ○ |
| Ex. 11 | Ethyl Acetate (50)/Acetone (50) | P (MMA-EMA) (5) | 3G (5) | Uniform | 12.0 | 10.9 | ○ |
| Ex. 12 | Ethyl Acetate (50)/Acetone (50) | P (MMA-EMA) (5) | TMPT (5) | Uniform | 14.0 | 11.5 | ○ |
| Ex. 13 | Ethyl Acetate (50)/Acetone (50) | P (MMA-EMA) (5) | 3G (2.5)/TMMT (2.5) | Uniform | 13.8 | 11.2 | ○ |
| Ex. 14 | Ethyl Acetate (50)/Acetone (50) | P (MMA-EMA) (5) | TMMT (0.1) | Uniform | 11.7 | 10.6 | ○ |
| C. Ex. 1 | Not Used | Not Used | Not Used | — | 6.9 | 2.5 | X |
| C. Ex. 2 | Ethyl Acetate (100) | Not Used | Not Used | Uniform | 8.8 | 4.2 | X |
| C. Ex. 3 | Ethyl Acetate (50)/Acetone (50) | Not Used | Not Used | Uniform | 8.6 | 4.1 | X |
| C. Ex. 4 | Ethyl Acetate (50)/Acetone (50) | P (MMA-EMA) (5) | Not Used | Whitened | 7.9 | 5.5 | Δ |
| C. Ex. 5 | Ethyl Acetate (50)/Acetone (50) | Not Used | TMMT (5) | Uniform | 10.5 | 5.2 | X |
| C. Ex. 6 | Ethyl Acetate (50)/Acetone (50) | P (MMA-EMA) (0.01) | TMMT (5) | Uniform | 10.5 | 5.5 | X |
| C. Ex. 7 | Ethyl Acetate (50)/Acetone (50) | P (MMA-EMA) (5) | TMMT (0.01) | Non-uniform | 7.9 | 5.6 | Δ |

Ex.: Example,
C. Ex.: Comparative Example

Next, the dental curable compositions of the present invention will be described more specifically with reference to Examples 15 to 44. However, the present invention shall not be limited to these Examples. Further, the following abbreviations were used for compounds used in Examples 15 to 26 and Comparative Examples 8 to 19. Further, combinations of the dental curable compositions of the present invention and the adhesive compositions of the present invention are shown in Examples 36 to 44. Monofunctional Radical Polymerizable Monomers:

M-AE-1;

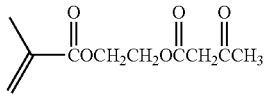

M-AE-5;

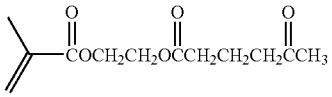

M-AE-6;

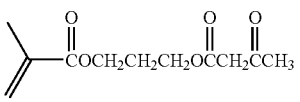

M-AE-7;

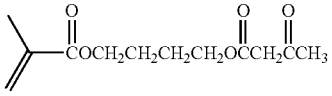

M-AE-8:

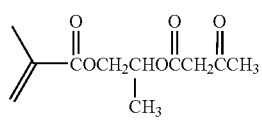

Difunctional Radical Polymerizable Monomers:
1;6-HD: 1,6-hexanediol dimethacrylate
1,9-ND: 1,9-nonanediol dimethacrylate Example 15

A solution was prepared by dissolving 0.025 parts by weight of methoxyhydroquinone as a polymerization inhibitor, 1 part by weight of diethyl-p-toluidine as a tertiary amine compound and 0.5 parts by weight of malic acid as a hydroxycarboxylic acid in 100 parts by weight of radical polymerizable monomer M-AE-1. 1 part by weight of benzoyl peroxide as an organic peroxide was dissolved in the solution so as to prepare a curable composition. Then, the prepared curable composition was poured into a mold for measuring a surface unpolymerized amount quickly to measure a surface unpolymerized thickness. As a result, the surface unpolymerized thickness was 77 μm.

The surface unpolymerized thickness was measured in accordance with the following measurement method (4).

(4) Measurement of Surface Unpolymerized Thickness

A polytetrafluoroethylene mold form having an external size of 25 mm in length and 25 mm in width, an internal size of 20 mm in length and 20 mm in width and a thickness of 1 mm was stuck on a polytetrafluoroethylene plate having a size of 30 mm in length and 30 mm in width and a thickness of 3 mm by use of an adhesive tape so as to prepare a measurement mold. The curable composition was poured into the mold and then polymerized and cured in an incubator kept at 37° C. with one surface of the curable composition exposed to the air. The obtained polymer was taken out of the mold, and its thickness was measured at 5 different locations by use of a micrometer so as to determine an average (D1). The cured product was immediately immersed in methanol for 1 minute, and a residual radical polymerizable monomer was removed. Then, after an insufficiently cured, soft layer was removed, the thickness of the cured product was measured at 5 different locations so as to determine an average (D2). D2–D1 was taken as a surface unpolymerized thickness of the cured product, and relative comparisons of curing properties were performed by use of the thickness.

Examples 16 to 26

Evaluations were made in the same manner as in Example 15 except that the type of the radical polymerizable monomer and the type and amount of the hydroxycarboxylic acid were changed as shown in Table 2. The results of measurements of the surface unpolymerized thicknesses of these curable compositions are also shown in Table 2.

Comparative Examples 8 to 15

Curable compositions were prepared in the same manner as in Example 15 except that no hydroxycarboxylic acid was added, and surface unpolymerized thicknesses thereof were measured. The results are shown in Table 2.

Comparative Examples 16 to 19

Samples were prepared and evaluations were made in the same manner as in Example 16 except that acids other than a hydroxycarboxylic acid were used in place of the hydroxycarboxylic acid. The results are shown in Table 2.

As shown in Table 2, Comparative Examples 8 to 15 containing no hydroxycarboxylic acid have surface unpolymerized thicknesses of 192 to 202 μm, while Examples 15 to 26 have surface unpolymerized thicknesses of 77 to 105 μm which are reduced to nearly ½ or less of the thicknesses of Comparative Examples 8 to 15. Thereby, the effect of adding hydroxycarboxylic acid compounds to the curable compositions of the present invention is obvious. Further, Comparative Examples 16 to 19 containing acids other than the hydroxycarboxylic acid have surface unpolymerized thicknesses of 195 to 202 μm, and it has been confirmed that addition of the acids other than the hydroxycarboxylic acid has no effect of reducing a surface unpolymerized amount.

TABLE 2

| | Radical Polymerizable Monomer 100 parts by weight | Acid Type | Amount (parts by weight) | Surface Unpolymerized Thickness (μm) |
|---|---|---|---|---|
| Ex. 15 | M-AE-1 | Malic Acid | 0.5 | 77 |
| Ex. 16 | M-AE-1 | Malic Acid | 0.1 | 102 |
| Ex. 17 | M-AE-1 | Malic Acid | 0.02 | 108 |
| Ex. 18 | M-AE-1 | Citric Acid | 0.1 | 115 |
| Ex. 19 | M-AE-1 | Tartaric Acid | 0.1 | 115 |
| Ex. 20 | M-AE-2 | Malic Acid | 0.1 | 108 |
| Ex. 21 | M-AE-3 | Malic Acid | 0.1 | 105 |
| Ex. 22 | M-AE-4 | Malic Acid | 0.1 | 96 |
| Ex. 23 | M-AE-5 | Malic Acid | 0.1 | 104 |
| Ex. 24 | M-AE-6 | Malic Acid | 0.1 | 99 |
| Ex. 25 | M-AE-7 | Malic Acid | 0.1 | 101 |
| Ex. 26 | M-AE-8 | Malic Acid | 0.1 | 104 |
| C. Ex. 8 | M-AE-1 | Not Used | | 192 |
| C. Ex. 9 | M-AE-2 | Not Used | | 205 |
| C. Ex. 10 | M-AE-3 | Not Used | | 201 |
| C. Ex. 11 | M-AE-4 | Not Used | | 193 |

TABLE 2-continued

| | Radical Polymerizable Monomer 100 parts by weight | Acid Type | Amount (parts by weight) | Surface Unpolymerized Thickness (μm) |
|---|---|---|---|---|
| C. Ex. 12 | M-AE-5 | Not Used | | 202 |
| C. Ex. 13 | M-AE-6 | Not Used | | 195 |
| C. Ex. 14 | M-AE-7 | Not Used | | 197 |
| C. Ex. 15 | M-AE-8 | Not Used | | 200 |
| C. Ex. 16 | M-AE-1 | Acetic Acid | 0.1 | 202 |
| C. Ex. 17 | M-AE-1 | Phosphoric Acid | 0.1 | 199 |
| C. Ex. 18 | M-AE-1 | Acrylic Acid | 0.1 | 197 |
| C. Ex. 19 | M-AE-1 | Methacrylic Acid | 0.1 | 195 |

Ex.: Example,
C. Ex.: Comparative Example

Example 27

A liquid component was prepared by dissolving 0.025 parts by weight of methoxyhydroquinone as a polymerization inhibitor, 1 part by weight of diethyl-p-toluidine as a tertiary amine compound and 0.5 parts by weight of malic acid as a hydroxycarboxylic acid compound in 100 parts. by weight of radical polymerizable monomer M-AE-1. Separately, a powder component was prepared by dispersing 0.6 parts by weight of benzoyl peroxide as an organic peroxide in 100 parts by weight of polyethyl methacrylate having an average particle diameter of 35 μm (weight average molecular weight: 500,000). Then, 1.6 parts by weight of the powder component was mixed and kneaded with 1 part by weight of the liquid component so as to prepare a paste. A surface unpolymerized thickness was evaluated in accordance with the same method as the evaluation method (4) of Example 15 except that the paste was used as a sample to be evaluated. As a result, the surface unpolymerized thickness was 63 μm which was a good result.

Examples 28 to 35

Evaluations were made in the same manner as in Example 27 except that the composition of the radical polymerizable monomer and the type and amount of the hydroxycarboxylic acid were changed as shown in Table 3. The results are also shown in Table 3.

Comparative Examples 20 to 22

Samples were prepared and surface unpolymerized thicknesses were measured in the same manner as in Example 27 except that radical polymerizable monomers shown in Table 3 were used and no hydroxycarboxylic acid was added. The results are also shown in Table 3.

Comparative Examples 23 to 26

Surface unpolymerized thicknesses were evaluated in the same manner as in Example 33 except that acids shown in Table 3 were used in place of the hydrocarboxylic acid. The results are also shown in Table 3.

As shown in Table 3, from comparisons of the results of Examples 27 to 35 with the results of Comparative Examples 20 to 22, an effect of reducing a surface unpolymerized thickness by addition of the hydroxycarboxylic acid was confirmed even in an agent of the type which required the liquid component prepared by dissolving the tertiary amine and the hydroxycarboxylic acid compound in the radical polymerizable monomer and the powder component prepared by dispersing the organic peroxide in the polymer powder to be mixed together right before use. Further, it was disclosed from comparisons of the results of Examples 27 to 35 with the results of Comparative Examples 23 to 26 that when acids other than the hydroxycarboxylic acid were used, a reduction in surface unpolymerized thickness was not observed and that this effect was exhibited only when the hydroxycarboxylic acid was added.

TABLE 3

| | Radical Polymerizable Monomer | | Acid | | Surface Unpolymerized |
|---|---|---|---|---|---|
| | Monofunctional (parts by weight) | difunctional (parts by weight) | Type | Amount (parts by weight) | Thickness (μm) |
| Ex. 27 | M-AE-1 (100) | Not Used | Malic Acid | 0.5 | 63 |
| Ex. 28 | M-AE-1 (100) | Not Used | Malic Acid | 0.1 | 85 |
| Ex. 29 | M-AE-1 (100) | Not Used | Malic Acid | 0.02 | 102 |
| Ex. 30 | M-AE-1 (50) | 1,6-HD (50) | Malic Acid | 0.5 | 49 |
| Ex. 31 | M-AE-1 (50) | 1,6-HD (50) | Malic Acid | 0.1 | 66 |
| Ex. 32 | M-AE-1 (50) | 1,6-HD (50) | Malic Acid | 0.02 | 94 |
| Ex. 33 | M-AE-1 (50) | 1,9-ND (50) | Malic Acid | 0.1 | 70 |
| Ex. 34 | M-AE-1 (50) | 1,6-HD (50) | Citric acid | 0.1 | 88 |
| Ex. 35 | M-AE-1 (50) | 1,9-ND (50) | Citric acid | 0.1 | 91 |
| C. Ex. 20 | M-AE-1 (100) | Not Used | Not Used | | 180 |
| C. Ex. 21 | M-AE-1 (50) | 1,6-HD (50) | Not Used | | 160 |
| C. Ex. 22 | M-AE-1 (50) | 1,9-ND (50) | Not Used | | 169 |
| C. Ex. 23 | M-AE-1 (50) | 1,6-HD (50) | Acetic Acid | 0.1 | 165 |

TABLE 3-continued

| | Radical Polymerizable Monomer | | Acid | | Surface Unpolymerized |
| | Monofunctional (parts by weight) | difunctional (parts by weight) | Type | Amount (parts by weight) | Thickness (μm) |
| --- | --- | --- | --- | --- | --- |
| C. Ex. 24 | M-AE-1 (50) | 1,6-HD (50) | Phosphoric Acid | 0.1 | 160 |
| C. Ex. 25 | M-AE-1 (50) | 1,6-HD (50) | Acrylic Acid | 0.1 | 167 |
| C. Ex. 26 | M-AE-1 (50) | 1,6-HD (50) | Methacrylic Acid | 0.1 | 165 |

Ex.: Example,
C. Ex.: Comparative Example

Examples 36 to 38

Evaluations were made in the same manner as in Example 1 except that compositions (adhesive compositions for denture base relining materials of the present invention) shown in Table 4 were used as adhesive compositions for denture base relining materials and that the curable composition used in Example 31 and comprising a powder component and a liquid component was used in place of TOKUSO REBASE FIRST TYPE as a denture base relining material. The results are also shown in Table 4.

Examples 39 to 41

Evaluations were made in the same manner as in Example 1 except that compositions shown in Table 4 were used as adhesive compositions for denture base relining materials and that the curable composition used in Example 33 and comprising a powder component and a liquid component was used as a denture base relining material. The results are also shown in Table 4.

Examples 42 to 44

Evaluations were made in the same manner as in Example 1 except that compositions shown in Table 4 were used as adhesive compositions for denture base relining materials and that the curable composition used in Example 34 and comprising a powder component and a liquid component was used as a denture base relining material. The results are also shown in Table 4.

Comparative Examples 27 to 35

Evaluations were made in the same manner as in Example 1 except that the curable compositions used in Examples 31, 33 and 34 were used and that either no adhesive composition for a denture base relining material was applied or compositions shown in Table 4 were used. Comparative Examples 27 to 29 use the curable composition used in Example 31, Comparative Examples 30 to 32 use the curable composition used in Example 33, and Comparative Examples 30 to 32 use the curable composition used in Example 34. The results of evaluations thereof are shown in Table 4.

TABLE 4

| | Composition (parts by weight) | | | | Surface Properties after Application | Adhesive Property (MPa) | | Evaluation of Durability |
| Ex. No. | Solvent | Polymer | Polymerizable Monomer | Used Curable Composition | | Initial | After Thermal Shock Test | |
| --- | --- | --- | --- | --- | --- | --- | --- | --- |
| Ex. 36 | Ethyl Acetate (50)/Acetone (50) | P (MMA-EMA) (5) | MMA (5) | Curable | Uniform | 13.5 | 12.3 | ○ |
| Ex. 37 | Ethyl Acetate (50)/Acetone (50) | P (MMA-EMA) (5) | TMPT (5) | Composition | Uniform | 15.8 | 13.5 | ○ |
| Ex. 38 | Ethyl Acetate (50)/Acetone (50) | P (MMA-EMA) (5) | TMMT (5) | Used in | Uniform | 16.3 | 13.3 | ○ |
| C. Ex. 27 | Not Used | Not Used | Not Used | Example 31 | — | 6.6 | 1.8 | X |
| C. Ex. 28 | Ethyl Acetate (50)/Acetone (50) | P (MMA-EMA) (5) | Not Used | | Whitened | 7.8 | 5.5 | Δ |
| C. Ex. 29 | Ethyl Acetate (50)/Acetone (50) | Not Used | TMMT (5) | | Uniform | 9.8 | 6.1 | Δ |
| Ex. 39 | Ethyl Acetate (50)/Acetone (50) | P (MMA-EMA) (5) | MMA (5) | Curable | Uniform | 14.2 | 12.8 | ○ |
| Ex. 40 | Ethyl Acetate (50)/Acetone (50) | p (MMA-EMA) (5) | TMPT (5) | Composition | Uniform | 16.7 | 13.9 | ○ |
| Ex. 41 | Ethyl Acetate (50)/Acetone (50) | P (MMA-EMA) (5) | TMMT (5) | Used in | Uniform | 16.5 | 13.8 | ○ |
| C. Ex. 30 | Not Used | Not Used | Not Used | Example 33 | — | 7.2 | 2.6 | X |
| C. Ex. 31 | Ethyl Acetate (50)/Acetone (50) | P (MMA-EMA) (5) | Not Used | | Whitened | 8.8 | 6.6 | Δ |
| C. Ex. 32 | Ethyl Acetate (50)/Acetone (50) | Not Used | TMMT (5) | | Uniform | 10.5 | 7.7 | Δ |
| Ex. 42 | Ethyl Acetate (50)/Acetone (50) | P (MMA-EMA) (5) | MMA (5) | Curable | Uniform | 13.1 | 10.8 | ○ |
| Ex. 43 | Ethyl Acetate (50)/Acetone (50) | P (MMA-EMA) (5) | TMPT (5) | Composition | Uniform | 15.3 | 12.1 | ○ |
| Ex. 44 | Ethyl Acetate (50)/Acetone (50) | P (MMA-EMA) (5) | TMMT (5) | Used in | Uniform | 14.8 | 12.5 | ○ |
| C. Ex. 33 | Not Used | Not Used | Not Used | Example 34 | — | 6.1 | 2.1 | X |
| C. Ex. 34 | Ethyl Acetate (50)/Acetone (50) | P (MMA-EMA) (5) | Not Used | | Whitened | 7.4 | 5.3 | Δ |
| C. Ex. 35 | Ethyl Acetate (50)/Acetone (50) | Not Used | TMMT (5) | | Uniform | 9.6 | 6.0 | Δ |

Ex.: Example.
C. Ex.: Comparative Example

As shown in Table 4, as a result of evaluating bonding of combinations of denture base relining materials comprising the curable compositions containing the radical polymerizable monomers having specific structures and the hydroxycarboxylic acids according to the present invention and the adhesive compositions for denture base relining materials according to the present invention to the material for a denture base, it is understood that they show bonding strengths of 13.1 to 16.7 MPa and show particularly excellent adhesive properties as compared with when other denture base relining materials were used (Examples 1 to 14). Further, it is also understood from comparisons of Example 36 with Comparative Examples of 27 to 29, comparisons of Example 39 with Comparative Examples of 30 to 32 or comparisons of Example 42 with Comparative Examples of 33 to 35 that the curable compositions for denture base relining materials of the present invention show excellent bonding strength and excellent bonding durability when the adhesive composition for a denture base relining material of the present invention comprising the polymer and the polymerizable monomer is used.

As described above, the adhesive composition for a denture base relining material of the present invention causes little environmental loads and exhibits low harmful effects since no organic solvent containing halogen atoms is used. Further, it has properties comparable to or better than those of conventional adhesives in terms of operability at the time of use, adhesive properties (bonding strength and bonding durability) and esthetics.

Further, the dental curable composition of the present invention containing the hydroxycarboxylic acid has a less surface unpolymerized amount than conventional materials. Thus, a cured product obtained from the composition hardly discolors and stains when used in an oral cavity. Further, the dental curable material of the present invention used in combination with the constitutional resin powder has increased viscosity due to dissolution of the resin compound, shows good operability at the time of use, and shows excellent strength after cured. In addition, by use of a monofunctional radical polymerizable monomer having a specific structure such as M-AE-1 and a multifunctional radical polymerizable monomer having an appropriate structure in combination as a radical polymerizable monomer, a material suitable as a material for. relining a denture base which emits little odor at the time of use and hardly causes irritations to hands, an oral membrane and the like can be provided.

The invention claimed is:

1. A dental curable composition comprising a radical polymerizable monomer, an organic peroxide, a tertiary amine and a hydroxycarboxylic acid, wherein the radical polymerizable monomer comprises a monofunctional (meth)acrylic ester represented by the following formula (1):

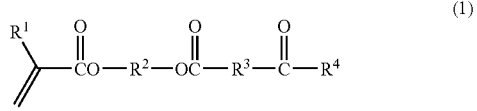

(1)

wherein $R^1$ is a hydrogen atom or a methyl group, $R^2$ and $R^3$ are each independently an alkylene group, and $R^4$ is an alkyl group.

2. The composition of claim 1, further comprising a polymer.

3. The composition of claim 1, comprising 100 parts by weight of the radical polymerizable monomer, 0.05 to 5 parts by weight of the organic peroxide, 0.05 to 5 parts by weight of the tertiary amine, and 0.005 to 2 parts by weight of the hydroxycarboxylic acid.

4. The composition of claim 1, wherein the radical polymerizable monomer is a combination of said monofunctional (meth)acrylic ester and a multifunctional (meth)acrylic ester.

5. A method of relining a denture base, which comprises the steps of:
applying an adhesive composition for a denture base relining material comprising 100 parts by weight of organic solvent containing no halogen atoms, 0.1 to 35 parts by weight of polymer, and 0.1 to 100 parts by weight of radical polymerizable monomer on a surface of a denture where the denture makes contact with an oral membrane so as to form a coating film comprising a polymer and a radical polymerizable monomer on the surface, and
applying and curing the composition of claim 1 or 2 on the coating film so as to form a prosthetic portion on the denture base.

6. A kit for relining a denture base which comprises a combination of a first container containing a mixture of a radical polymerizable monomer, a tertiary amine, and a hydroxycarboxylic acid and a second container containing a mixture of polymer and an organic peroxide, wherein the radical polymerizable monomer comprises a monofunctional (meth)acrylic ester represented by the following formula (1):

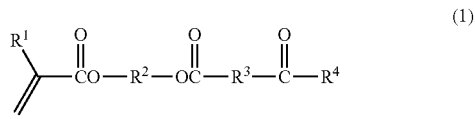

(1)

wherein $R^1$ is a hydrogen atom or a methyl group, $R^2$ and $R^3$ are each independently an alkylene group, and $R^4$ is an alkyl group.

7. The kit of claim 6, further comprising a third container containing an adhesive composition for a denture base relining material comprising 100 parts by weight of organic solvent containing no halogen atoms, 0.1 to 35 parts by weight of polymer, and 0.1 to 100 parts by weight of radical polymerizable monomer.

8. The composition of claim 4, wherein the multifunctional (meth)acrylic ester is a difunctional (meth)acrylic ester and the weight ratio of the monofunctional (meth)acrylic ester to the difunctional (meth)acrylic ester is between 5:95 and 95:5.

* * * * *